United States Patent
Demos et al.

(10) Patent No.: US 7,587,236 B2
(45) Date of Patent: Sep. 8, 2009

(54) OPTICAL SPECTROSCOPY FOR THE DETECTION OF ISCHEMIC TISSUE INJURY

(75) Inventors: Stavros Demos, Livermore, CA (US); Jason Fitzgerald, Sacramento, CA (US); Christoph Troppmann, Sacramento, CA (US); Andromachi Michalopoulou, Athens (GR)

(73) Assignee: Lawrence Livermore National Security, LLC, Livermore, CA (US)

( * ) Notice: Subject to any disclaimer, the term of this patent is extended or adjusted under 35 U.S.C. 154(b) by 427 days.

(21) Appl. No.: 11/031,936

(22) Filed: Jan. 8, 2005

(65) Prior Publication Data
US 2005/0171414 A1 Aug. 4, 2005

Related U.S. Application Data

(60) Provisional application No. 60/535,585, filed on Jan. 8, 2004, provisional application No. 60/559,887, filed on Apr. 5, 2004.

(51) Int. Cl.
*A61B 6/00* (2006.01)
(52) U.S. Cl. .................. 600/477; 600/473; 600/476
(58) Field of Classification Search .............. 600/309, 600/310, 322, 323, 341, 472, 476
See application file for complete search history.

(56) References Cited

U.S. PATENT DOCUMENTS

| | | |
|---|---|---|
| 5,413,108 A | 5/1995 | Alfano |
| 5,685,313 A | 11/1997 | Mayevsky |
| 5,701,902 A | 12/1997 | Vari et al. |
| 5,847,394 A | 12/1998 | Alfano et al. |
| 5,916,171 A | 6/1999 | Mayevsky |
| 6,124,597 A | 9/2000 | Shehada |
| 6,825,928 B2 * | 11/2004 | Liu et al. ............ 356/317 |
| 2004/0054270 A1 | 3/2004 | Pewzner et al. |

OTHER PUBLICATIONS

Demos S. G. et al: "Cancer detection using NIR elastic light scattering and tissue fluorescence imaging". Conference on Lasers and Electro-Optics. (Cleo 2001). Technical Digest. Post conference edition. Baltimore, MD, May 6-11, 2001, Trends in Optics and photonics. (TOPS), US, Washington, WA: OSA, US, vol. vol. 56, May 6, 2001, pp. 361-362, XP010559944 ISBN: 1-55752-662-1.

* cited by examiner

*Primary Examiner*—Eric F Winakur
*Assistant Examiner*—Michael T Rozanski
(74) *Attorney, Agent, or Firm*—John Wooldridge; Michael C. Staggs; John H. Lee (57) ABSTRACT

An optical method and apparatus is utilized to quantify ischemic tissue and/or organ injury. Such a method and apparatus is non-invasive, non-traumatic, portable, and can make measurements in a matter of seconds. Moreover, such a method and apparatus can be realized through optical fiber probes, making it possible to take measurements of target organs deep within a patient's body. Such a technology provides a means of detecting and quantifying tissue injury in its early stages, before it is clinically apparent and before irreversible damage has occurred.

54 Claims, 5 Drawing Sheets

OPTICAL SPECTROSCOPY FOR THE DETECTION OF ISCHEMIC TISSUE INJURY

RELATED APPLICATION

This application claims the benefit of U.S. Provisional Application No. 60/535,585, filed Jan. 8, 2004, and U.S. Provisional Application No. 60/559,887, filed Apr. 5, 2004, both entitled, "Optical Spectroscopy for the Detection of Ischemic Tissue Injury," which is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to a medical diagnostic for investigating tissue components. More particularly, the present invention relates to an apparatus and a method that utilizes autofluorescence emission and/or polarized elastic light scattering as an interrogation means for investigating tissue states for medical applications.

2. Description of Related Art

Transplant surgeons often face the difficult question of whether organs from a cadaveric donor are suitable for transplantation. It is currently difficult to quantify how much warm ischemic organ damage has occurred, especially if a donor has experienced significant hemodynamic instability. Organ procurement in brain-dead and non-heart-beating donors can cause a variable amount of additional warm ischemia. Transplanting organs that have sustained significant pre-implantation warm ischemic damage may leave the recipient with unacceptably poor allograft function and adversely affect graft and patient survival. On the other hand, as transplant waiting lists continue to grow, it becomes increasingly important to maximize utilization of viable organs from marginal donors.

Post transplant monitoring is currently the only reliable way of assessing ischemic organ damage; unfortunately, at that stage the organ is already in the recipient and may have to be removed if found to be nonviable. Three fundamental questions regarding ischemia in a transplanted organ are apparent. First, how much ischemic damage has an organ sustained? Second, how does the organ respond to intervention aimed at halting or reversing ischemic damage? Third, how will the organ function after it is transplanted? Beneficial methods and apparatus for analyzing organ ischemia and answering such questions is needed at any stage of transplantation, while the organ is still in the donor, after it has been removed (during hypothermic preservation), while it is being implanted, and after reperfusion. Such methods and apparatus require real-time, substantially instantaneous results so that clinical decisions can be made in a timely fashion.

Background information on an existing approaches that addresses organ damage is described by Inman S., Osgood R., Plott W., et al., in "*Identification of kidneys subjected to pre-retrieval warm ischemic injury during hypothermal perfusion preservation*," Transplant Proc., 1998, pp. 42-46, and in "*The non heart-beating donor*," by Kootstra G., Kievet J K, Heineman E., Br Med Bull., (1997); 53 (4): 844, and in "*Release of alpha-glutathione S-transferase (alpha GST) and pi-glutathione S-transferase (pi GST) from ischemic damaged kidneys into the machine perfusate-relevance to viability assessment*," Transplant Proc. (1997); 29 (8): 3591. However, such approaches are hindered by clinical practicality as well as by hypothermic preservation.

Background information on monitoring tissue viability is described and claimed in U.S. Pat. No. 2004/0054270 A1, entitled "Apparatus And Method For Monitoring Tissue Vitality Parameters," issued Mar. 18, 2004 to Pewzner et al., including the following, "Apparatus for monitoring a plurality of tissue viability parameters of a tissue layer element, in which two different illumination sources are used via a common illumination element in contact with the tissue. One illumination source is used for monitoring blood flow rate and optionally flavoprotein concentration, and collection fibers are provided to receive the appropriate radiation from the tissue. The other illuminating radiation is used for monitoring any one of and preferably all of NADH, blood volume and blood oxygenation state of the tissue element, and collection fibers are provided to receive the appropriate radiation from the tissue." However, such techniques from the above cited patent does not address detecting and quantifying ischemic tissue damage in its incipient stages in accordance with the principles of the present invention.

Accordingly, a need exists for methods and apparatus that can detect and quantify tissue parameters in its early stages before injury is clinically apparent and before irreversible damage has occurred. The present invention is directed to such a need.

SUMMARY OF THE INVENTION

Accordingly, the present invention is directed to a method for assessing tissue parameters, including: illuminating a tissue component region with a first substantially narrow spectral band source; illuminating the tissue component region with a second substantially narrow spectral band source, wherein the illuminated region by the first and said second substantially narrow spectral band sources comprises an area of greater than about 1.5 $mm^2$; detecting a respective autofluorescence emission from the illuminated region induced by the first and the second substantially narrow spectral band sources; and comparing intensities of the respective autofluorescence emission to assess in real-time, at least one parameter selected from: tissue properties, the metabolic state, injury, and tissue property changes resulting from therapeutic or prophylactic intervention of the tissue component region.

Another aspect of the present invention provides an apparatus for assessing tissue parameters that includes inducing autofluorescence in a same tissue component region with a source beam area of greater than about 1.5 $mm^2$ and comparing intensities of recorded autofluorescence emission from the same tissue component region to assess in real-time, at least one parameter selected from: tissue properties, the metabolic state, injury, and tissue property changes resulting from therapeutic or prophylactic intervention of the tissue component region.

Still another aspect of the present invention is an apparatus for assessing tissue parameters that includes inducing autofluorescence in a same tissue component region with a laser source beam area of greater than about 1.5 $mm^2$. Such a source can be directed by an optical fiber bundle having a sheath for registering tissue components with the distal end of the fiber bundle, wherein intensities of recorded autofluorescence received by the fiber bundle from the same tissue component region are compared to assess in real-time, at least one parameter selected from: tissue properties, the metabolic state, injury, and tissue property changes resulting from therapeutic or prophylactic intervention of the tissue component region.

Accordingly, the present provides optical arrangements and methods, capable of directing predetermined spectral radiation and capable of providing received spectral information for the assessment in real-time of desired tissue parameters. Applications include, but are not limited to, assessment of tissue viability in clinical environments, rapid assessment of tissue viability in civilian and battlefield trauma scenarios, solid organ transplant, cerebrovascular disease, cardiovascular disease, diabetic tissue injury and ischemic bowel disease.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Referring now to the drawings, specific embodiments of the invention are shown. The detailed description of the specific embodiments, together with the general description of the invention, serves to explain the principles of the invention.

General Description

The present invention provides apparatus and methods for real-time determination and quantification of the state of tissue components. In general, the apparatus as disclosed herein, can include an optical probe having at least one illumination optical fiber, a plurality of collection optical fibers, at least one radiation source so as to cause scattering and/or photo-excitation so as to induce autofluorescence in a targeted tissue component; a detector system that acquires such autofluorescence and scattered spectra of polarized and unpolarized light; and a processor primarily arranged for comparing received autofluorescence signals so as to assess in real-time tissue properties, the metabolic state, injury, and tissue property changes resulting from therapeutic or prophylactic intervention of tissue components, such as, but not limited to brain, kidney, liver, heart, bowel, stomach, skin, pancreas, and muscle.

Specific Description

Figure 1:
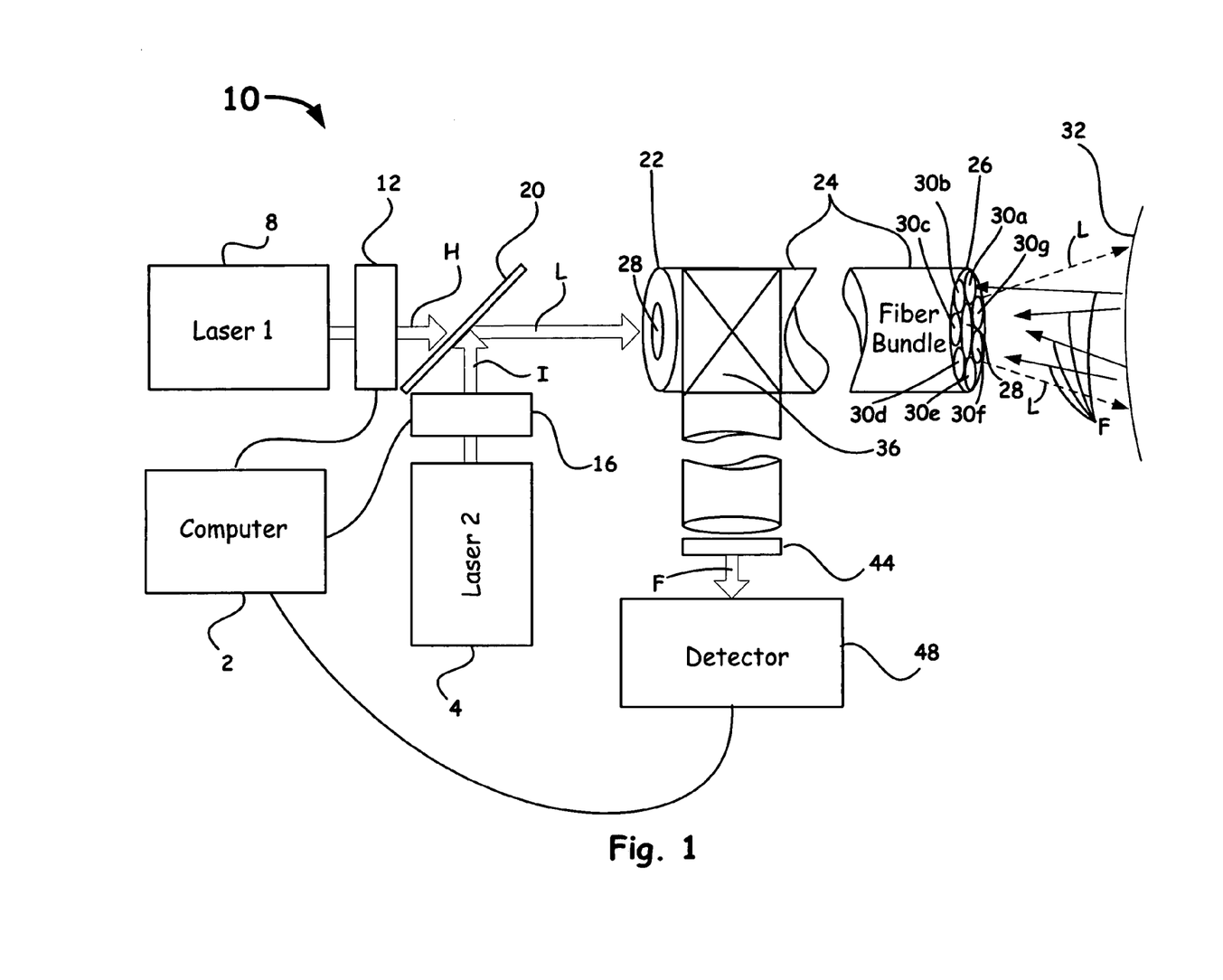
FIG. 1 shows a simplified diagram of diagnostic apparatus to determine desired tissue parameters.

Turning now to the drawings, a diagram that illustrates an exemplary embodiment of a system constructed in accordance with the present invention is shown in FIG. 1. The system, designated generally by the reference numeral 10, and capable of being designed as a portable compact apparatus, includes the following basic components: a processor 2, such as, but not limited to, a desktop computer, a laptop computer, a Personal Digital Assistant (e.g. a handheld personal computer), or any processing unit capable of handling the data of the present invention; one or more sources of electromagnetic radiation 4, 8 having a known intensity and having an emission wavelength of at least 250 nm; optical shutters 12, 16; optical element 20; and a radiation conduit 24 (e.g., an optical fiber bundle) adapted to direct transmitted and collected induced autofluorescence and/or a scattered desired radiation from tissue components 32 through one or more optical filters 44, such as edge filters, band-pass filters, polarization filters, and/or notch filters, to allow desired bands and polarized components of electromagnetic radiation from tissue components 32 to be recorded by one or more detectors 48.

Electromagnetic radiation sources 4, 8 can be configured to emit a spectral band along paths H, I (shown with accompanying arrows), upon activation of electronically or mechanically driven shutters 12, 16, as shown in FIG. 1. Although radiation sources 4, 8 can include a broad-band white light lamp capable of emitting filtered excitation radiation to interact with desired tissue components 32 (e.g., by long pass, band-pass, narrow-band pass filters, etc.), such sources are more often a monochromatic optical source, such as, a pulsed and/or a CW (continuous wave) laser, having desired power output levels of at least 1 mW, and often having wavelengths of at least 250 nm, more often a wavelength range between about 260 nm and about 360 nm, and even more often a 360 nm and/or a 335 nm wavelength.

Although several commercially available types of laser systems can be employed in practice of the invention, an exemplary system often includes an optical parametric oscillator, (i.e., a nonlinear material capable of producing a coherent beam of light that can be tuned over a wide range of wavelengths) to obtain the required power levels and wavelengths as required. However, any lasing apparatus, such as diode lasers, dye lasers, tripled Nd:Yag systems, etc., having sufficient spectral bandwidth and power levels, and geometry to be integrated with the present invention may be utilized without departing from the spirit and scope of the present invention.

Optical element 20, such as, for example, an e-beam deposited beam-splitter, a liquid crystal splitter, an electro-optic device, an acousto-optic device, a mechanically driven reflective devices, and/or a predetermined dichroic mirror, is arranged to receive the radiation and direct such radiation along a beam path denoted by the letter L, also shown with an accompanying arrow.

Directed radiation L is then received by a proximal end 22 of a radiation conduit 24, e.g., an optical fiber bundle that includes a predetermined illumination optical fiber 28 and one or more collection optical fibers 30a-30g housed in a cable. Laser radiation L passes through fiber 28 and is directed through to a distal end 26 so as to substantially and uniformly illuminate (shown as dashed arrows and denoted by the letter L) a desired tissue component 32 region with an illumination area of at least greater than 1.5 mm$^2$. Optical fibers 30a-30g are configured to collect scattered and/or induced autofluorescence (shown as solid arrows and denoted by the letter F) resulting from radiation L and are directed back through fibers 30a-30g, toward proximal end 22 and redirected along a routed path 36 through a filter 44, (shown as letter K) such as, for example, an analyzing polarizer such that parallel, linear polarization, orthogonal cross-polarization, orthogonal elliptical polarization, same elliptical polarization, opposite circular polarization, or non-polarization analysis of the autofluorescence emission or scattered radiation F may be employed.

In addition, a spectral pass filter, such as, but not limited to, a long pass filter to ensure a proper spectral band selection between about 290 nm and about 1000 nm can also be positioned as filter 44 to collect a desired spectral radiation. Upon such filtering, the collected radiation can be recorded by detector 48, such as, for example, a photodiode, a photomultiplier, a spectrometer, a pixilated imaging sensor, a charge coupled device (CCD), and/or any imaging device constructed to the design output parameters for system 10 and processed in real-time by, for example, a computer 2 in determining and quantifying a desired tissue component and/or organ state.

Figure 2:
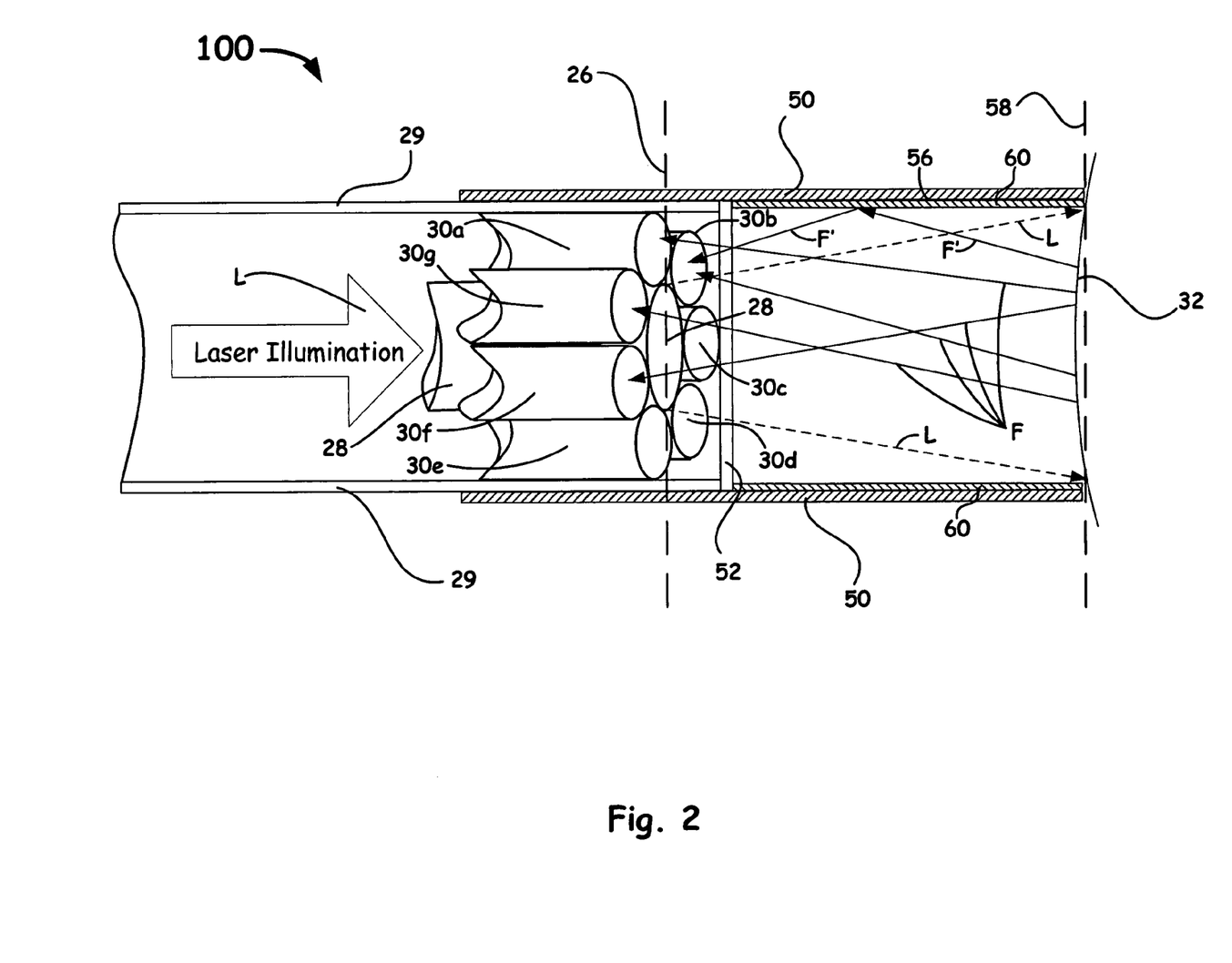
FIG. 2 shows an enlarged view of an example radiation conduit of the present invention.

FIG. 2 shows another example radiation conduit, i.e., an optical fiber assembly, generally designated as reference numeral 100, in more detail. As illustrated, laser illumination L (as shown by the enlarged directional arrow) can be directed through optical fiber 28, shown enclosed in a housing 29 with adjacent collection optical fibers 30a-30g, so as to illuminate tissue 32. The collected scattered and/or induced fluorescence radiation F then passes in a backscattered geometry, through optical fibers 30a-30g each having, for example, a 100 micron core diameter with predetermined separation gaps of at least about 0.20 mm so as to direct received radiation to detector 48, as discussed above, and as shown in FIG. 1.

A beneficial feature of the arrangement shown in FIG. 2 is a sheath 50, configured to position distal end 26 (shown as a dashed line) of optical fibers 28 and 30a-30g with respect to tissue 32 by bringing in to registry sheath 50 with tissue 32 (shown at dashed line 58). Moreover, sheath 50, can be configured with an ultra violet transmissive window 52, disposed within interior wall 56 to enable wavelengths greater than about 190 nm to be transmitted by fiber 28 for illumination of tissue 32 components. In addition, window 52 operates with sheath 50 to enclose and protect optical fibers 28 and 30a-30g from tissue contamination. Moreover, sheath 50 can be arranged with one or more additional optical elements (not shown) disposed within interior wall 56, such as, diffractive optical components (lenses) and/or filters (polarization filters, long-pass filters, band-pass filters, etc.) to efficiently deliver desired beam characteristics and radiation properties (e.g., bandwidth and polarization) from sources 4, 8, to tissue components 32.

An additional beneficial example feature of sheath 50 is a reflective surface 60 to radiation induced from tissue 32, wherein a ray path outside of the acceptance angle of collection fibers 30a-30g, such as ray F', as shown in FIG. 2, can be internally reflected and collected by, for example, fiber 30b. Such a reflective feature can be produced, for example, by having sheath 50 arranged with a deposited reflective coating 56, such as, by vacuum deposition, CVD, e-beam deposition, or any method known to those skilled in the art capable of producing such a coating or by for example, manufacturing sheath 50 from a material, such as a metal and having its interior wall polished so as to increase collection efficiency for predetermined wavelengths induced by illumination wavelength L.

The combined investigative approach method embodiment of polarized light scattering and/or biological fluorophore autofluorescence ratios using the apparatus, as discussed above, includes the following techniques.

Autofluorescence

Fluorophores in biological tissue, such as but not limited to, tryptophan, collagen, elastin, and NAD (nicotinamide adenine dinucleotide) emit fluorescence when illuminated with radiation. NAD, in particular, is at much lower concentrations within tissue components, such as in humans, and consequently provides for low level emission intensity when subjected to an excitation wavelength relative to other fluorophores.

However, the intrinsic mitochondrial fluorophore, nicotinamide adenine dinucleotide (NADH), exhibits a peak in its emission spectrum at about 470-nm when excited at a wavelength within its absorption spectrum, e.g., 335-nm, and is therefore likely the molecule responsible for the changing spectroscopic properties associated with certain tissue states in humans or animals, e.g., ischemia and hypoxia. During cellular respiration, NAD is reduced to NADH to serve as an electron transporter in the oxygen dependent process that regenerates the cellular energy unit ATP. Without oxygenated blood flow, NADH accumulates in tissue and causes an increase in autofluorescence when excited with the appropriate wavelength. Therefore, fluorescence from probed, for example, "injured" tissue components having such a fluorophore results in a rise in intensity of a fluorescence spectrum resulting from an increase in the induced NADH. Unlike NADH, certain predetermined biological fluorophores, such as, tryptophan, is not directly involved in aerobic or anaerobic cellular respiration. Accordingly, the spectroscopic properties of tryptophan is "inert", i.e., induced autofluorescence is insensitive to tissue parameters, such as, but not limited to, ischemia.

The present invention provides a beneficial use of such fluorescence properties by comparing NADH fluorescence emission induced by an absorbing wavelength within the NADH spectrum to the relative fluorescence of a predetermined fluorophore, e.g., Tryptophan, produced by an absorbing wavelength within such a flurophore's absorption spectrum.

Specifically, by comparing autofluorescence intensity at 335-nm, which changes with tissue property states, such as a tissue component in the state of ischemia, with autofluorescence of, for example, tryptophan, induced by 260-nm excitation in the same area, parameters, such as tissue properties, the metabolic state, injury, and tissue property changes resulting from therapeutic or prophylactic intervention of probed tissue components can be realized in real-time, e.g., less than about a minute.

Another beneficial arrangement is to produce standards from predetermined tissue components based on, for example, but not limited to, a persons age, sex, weight, and race to be stored by a processor or other means so as to normalize compared signals as discussed above and enhance the analysis capabilities of the present invention.

Elastic Light Scattering

Another example embodiment of the present invention is the incorporation of polarized elastic light scattering to additionally assess tissue characteristics to allow an end-user to acquire clinical diagnostic deep-subsurface (e.g., at least 1 cm) images in collaboration with the autofluorescence method as discussed above. An illumination wavelength from an electromagnetic radiation source can be utilized to provide a predetermined mean photon penetration depth larger. Linear cross-polarization and spectral analysis of the scattered photons substantially removes the photon information from the orthogonal illumination polarization resulting from the surface and allows substantially all of the scattered photons from the subsurface tissue to be imaged.

In addition, a spectral polarization difference technique (SPDI) can be utilized in the present invention. Such a similar method is disclosed in pending U.S. application Ser. No. 10/190,231, titled "Near Infrared Spectroscopic Tissue Imaging In Medical Applications," by Demos et al., the disclosure which is herein incorporated by reference in its entirety. With SPDI, different illumination wavelengths are utilized to record, for example, images having a differential mean photon penetration depth. Thus, smaller differential illumination wavelengths can provide a narrower differential depth zone while a larger difference in two exemplary illuminating wavelengths gives rise to a wider depth zone. Cross-polarization and normalization analysis coupled with inter-image operations such as but not limited to subtraction between one or more illuminating wavelengths can provide information as to the tissue structure between the penetration depths of the one or more respective probe illumination wavelengths. The present invention uses such a technique in addition to comparing autofluorescence and light scattering intensity measurements, such as single wavelength cross-polarized light scattered measurements from the same predetermined tissue component regions for analysis of tissue parameters as discussed herein.

An exemplary prototype apparatus and experiments were constructed and performed at the UC Davis Medical Center in Sacramento, Calif. The following data are used to only illustrate some of the novel capabilities of the present invention.

Figure 3A:
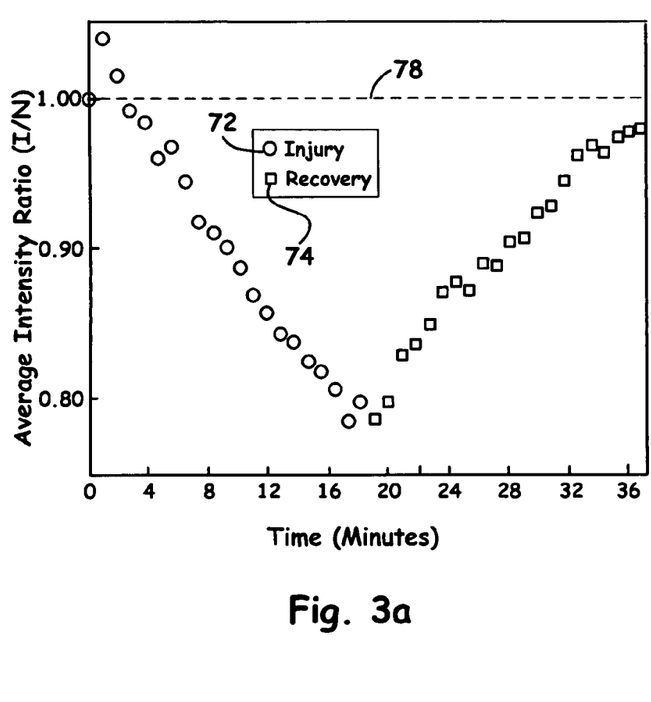
FIGS. 3a and 3b, illustrates real-time injured (i.e., kidney tissue in a state of ischemia) to normal (control kidney tissue) autofluorescence intensity measurements.
Figure 3B:
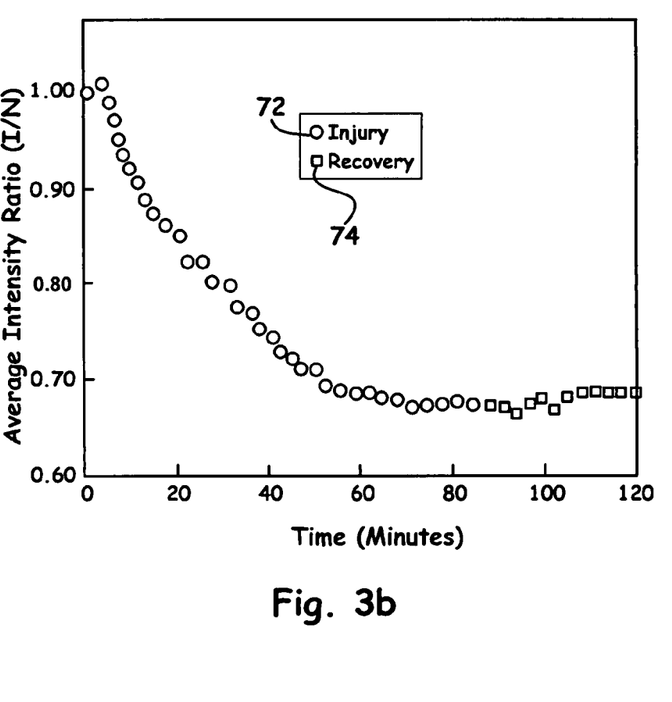

FIGS. 3a and 3b, illustrates capabilities of the present invention wherein real-time injured (i.e., kidney tissue in a state of ischemia) to normal (control kidney tissue) autofluorescence intensity ratios are measured. Such measurements includes 335 nm excitation imaged through a 450 nm narrow band filter, of in-vivo kidneys made ischemic 72 (symbolized as circles) for 20 minutes, as shown in FIG. 3a, and 90 minutes, as shown in FIG. 3b and subsequently reperfused (symbolized as squares).

Specifically, FIGS. 3a and 3b, illustrates real-time, in-vivo experiments in anesthetized rats with exposed kidneys. Injured kidneys underwent clamping to cause injury 72 of their vascular pedicles for 20 minutes, as shown in FIG. 3a or 90 minutes, as shown in FIG. 3b, followed by unclamping and a recovery phase 74. Kidneys ischemic for 20 minutes exhibited a recovery rebound of intensity toward a baseline 78, as shown in FIG. 3a, whereas kidneys injured for 90, as shown in FIG. 3b, minutes did not exhibit any recovery of intensity.

Figure 4:
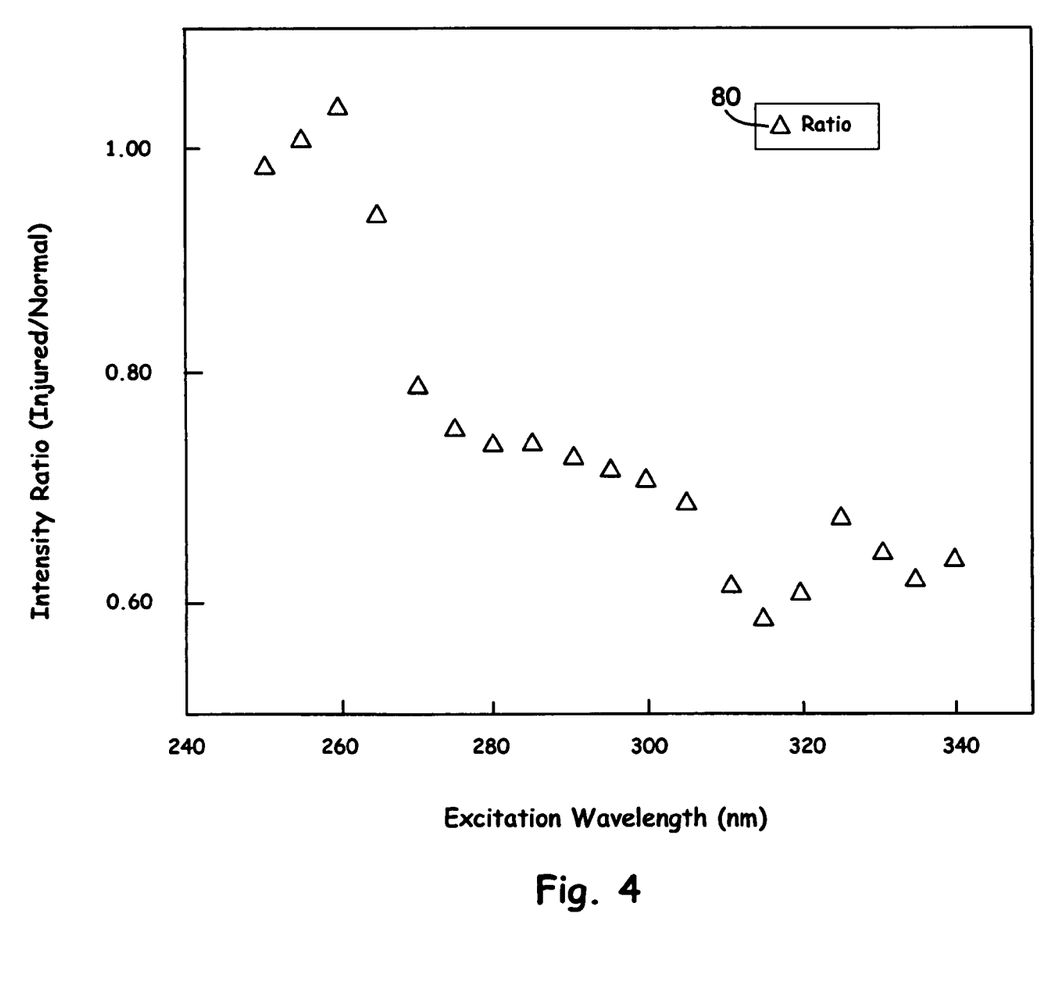
FIG. 4 shows intensity data measurements from about 240 nm to about 340 nm.

FIG. 4 illustrates expansion of the autofluorescence techniques of the present invention using other excitation wavelengths in the UV spectral region (i.e., from about 240 nm to about 340 nm). Specifically, FIG. 4 shows Injured to normal intensity ratios 80 (symbolized as triangles), using various excitation wavelengths and imaged through a 395 long pass filter, for kidneys undergoing 60 minutes of ischemic damage. At 260 nm excitation, the injured to normal intensity ratio is 1.

In effect, FIG. 4 illustrates a novel and beneficial embodiment of the present invention wherein an injured kidney appears inert when analyzed by 260 nm. Thus, instead of using an injured to uninjured intensity ratio, as shown in FIGS. 3a and 3b, as a measurement of ischemia in an injured kidney, 335 nm to 260-nm excitation ratio from an injured kidney alone, as shown in FIG. 4, can be utilized as a method for real-time assessment of the state of a tissue component and/or organ. By utilizing such a comparison method, coupled with techniques described herein, the present invention can rapidly assess tissue parameters as stated above.

Figure 5A:
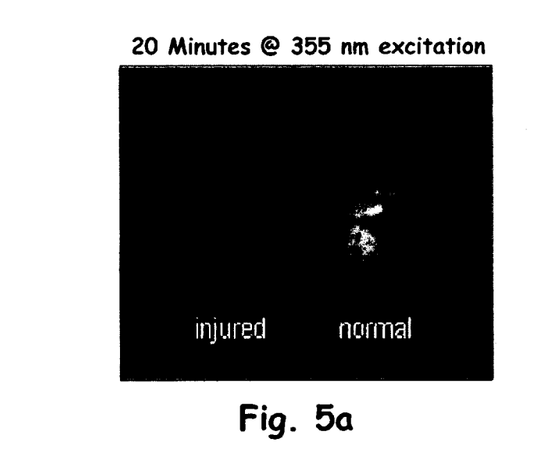
FIGS. 5a-d shows a series of fluorescence images collected by the present invention.
Figure 5B:
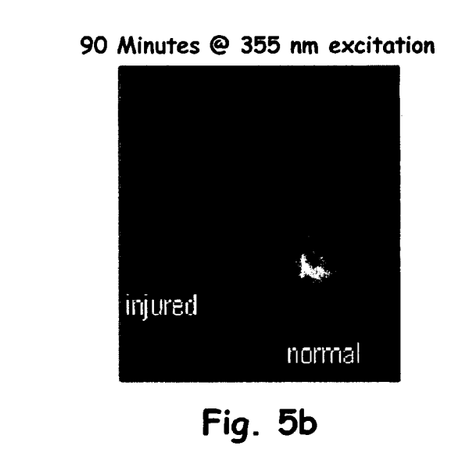
Figure 5C:
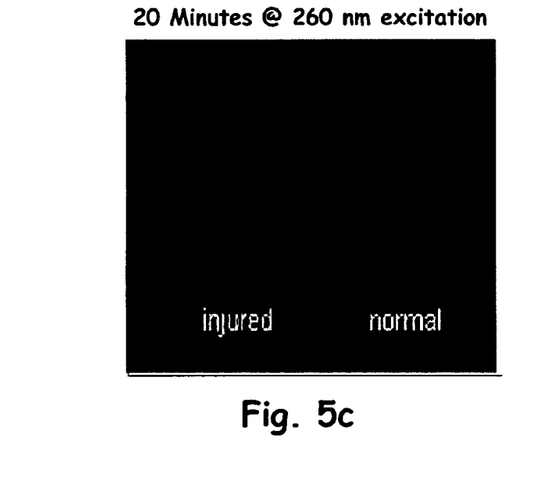
Figure 5D:
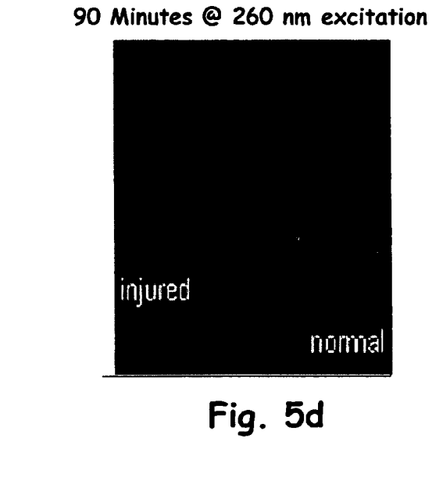

FIGS. 5a, 5b, 5c and 5c further illustrates the method of the present invention with a set of injured and normal kidney intensity images taken through a 395 long-pass filter under 335-nm and 260-nm excitation. As predicted by the data in FIG. 4, obvious differences in intensity due to 20 minutes, as shown in 5a and 5c, and 90 minutes as shown in 5b and 5d, of ischemic injury under 335-nm excitation, as shown in 5a and 5b, disappear under 260-nm excitation, as shown in 5c and 5d.

Another beneficial method of the present invention involves monitoring fluorescing contrast agents infused in various organs and/or tissue by arterial circulation in situ using the methods and apparatus of the present invention. Alternatively, such contrast agents can be infused in, for example, an organ, through a perfusion pump. The amount of such contrast agents remaining in a tissue component region or organ after a given period of time is proportional to the amount of capillary permeability and thus to the degree of the state of a tissue, e.g., ischemia. Using techniques and apparatus described herein coupled with utilized contrast agents provides a quantifiable measurement of desired tissue parameters.

Still another beneficial arrangement of the present invention is to illuminate with a set of wavelengths, preferably two, and image a predetermined component region. The objective is to employ hyperspectral (i.e., using various spectroscopic techniques and multiple wavelength and/or spectral bands) imaging to investigate the ability of polarized light in combination with predetermined tissue component autofluorescence so as to also assess in real-time, tissue properties, the metabolic state, injury, and tissue property changes resulting from therapeutic or prophylactic intervention of said tissue component region.

Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The invention claimed is:

1. A method, comprising:
    illuminating a surface area of tissue with a first beam of light from a first substantially narrow spectral band source to produce an illuminated surface area, wherein said first beam of light is delivered from the distal end of an illumination transporting optic, including said distal end, wherein said distal end does not make contact with said tissue, wherein said illuminated surface area is larger than about 1.5 mm$^2$, wherein said first beam of light induces a first autofluorescence emission from said surface area;
    illuminating at least part of said surface area with a second beam of light from a second substantially narrow spectral band source, wherein said second beam of light is delivered from said distal end, wherein said second beam of light induces a second autofluorescence emission from said surface area;
    detecting said first autofluorescence emission and said second autofluorensense emission; and
    comparing said first autofluorescence emission to said second autofluorensense emission to assess in real-time a property of said tissue.

2. The method of claim 1, wherein said first autofluorescence emission and said second autofluorescence from said tissue are within a spectral region between about 400 nm and about 1000 nm.

3. The method of claim 1, wherein said first autofluorescence emission and said second autofluorescence from said tissue are within a spectral region between about 290 nm and about 800 nm.

4. The method of claim 1, wherein said first autofluorescence emission and said second autofluorescence emission comprise an emission from a biological fluorophore.

5. The method of claim 1, wherein said first substantially narrow spectral band source and said second substantially narrow spectral band source comprise a monochromatic light source.

6. The method of claim 5, wherein said monochromatic light source can emit a wavelength of at least 250 nm.

7. The method of claim 5, wherein at least one of said first substantially narrow spectral band source and said second substantially narrow band source provides a wavelength within the absorption spectrum of NADH.

8. The method of claim 5, wherein at least one of said first substantially narrow band source and said second substantially narrow spectral band source provides a wavelength within the absorption spectrum of tryptophan.

9. The method of claim 1, wherein at least one of said first substantially narrow spectral band source and said second substantially narrow spectral band source is produced from a broad band lamp designed to transmit predetermined filtered wavelengths.

10. The method of claim 1, wherein said illumination transporting optic comprises an optical fiber bundle configured to substantially illuminate an area having a long dimension of up to about 10 cm.

11. The method of claim 10, wherein said optical fiber bundle is adapted for receiving a scattered radiation and said autofluorescence.

12. The method of claim 1, wherein the step of detecting comprises hyperspectral microscopy imaging of tissue microstructure and assessing microscopic alterations associated with tissue injury.

13. The method of claim 1, wherein said tissue is in a state of ischemia.

14. The method of claim 1, wherein said tissue is in a state of hypoxia.

15. The method of claim 1, wherein said first substantially narrow spectral band source and second substantially narrow spectral band source are polarized.

16. The method of claim 1, wherein said first substantially narrow spectral band source and second substantially narrow spectral band source are linearly polarized and a parallel-polarized component of at least one of said first autofluorescence emission or said second autofluorescence emission is analyzed.

17. The method of claim 16, wherein a perpendicularly polarized component of at least one of said first autofluorescence emission or said second autofluorescence emission is analyzed.

18. The method of claim 1., wherein one of said first autofluorescence emission or said second autofluorescence emission comprises an opposite circular polarization orientation with respect to said first substantially narrow spectral band source and said second substantially narrow spectral band source, said method further comprising analyzing said opposite circular polarization orientation.

19. The method of claim 1, wherein said first substantially narrow spectral band source and said second substantially narrow spectral band source are elliptically polarized and a same elliptical polarization orientation of said first autofluorescence emission and said second au tofluorescence emission is analyzed.

20. The method of claim 19, wherein an orthogonal elliptical polarization of at least one of said first autofluorescence emission or said second autofluorescence is analyzed.

21. The method of claim 1, wherein said first substantially narrow spectral band source and said second substantially narrow spectral band source are polarized and a scattered electromagnetic radiation is analyzed.

22. The method of claim 21, wherein an orthogonal polarization component of said scattered electromagnetic radiation is analyzed.

23. The method of claim 1, wherein the detecting step is carried out with a charge coupled device.

24. The method of claim 1, wherein the detecting step is carried out with a device selected from the group consisting of a photomultiplier and a photodiode.

25. The method of claim 1, wherein said tissue is selected from the group consisting of brain, kidney, liver, heart, bowel, skin, stomach, pancreas, and muscle.

26. The method of claim 1, further comprising infusing a fluorescing contrast agent into said tissue to determine a quantifiable measurement of tissue injury.

27. An apparatus for assessing tissue parameters, comprising:
a first source of electromagnetic radiation configured to produce a first beam of light having a substantially narrow spectral band;
a second source of electromagnetic radiation configured to produce a second beam of light having a substantially narrow spectral band;
an illumination transporting optic, comprising a distal end, wherein said conduit is adapted for directing said first beam of light and said second beam of light to illuminate from said distal end, a surface area of a tissue to produce an illuminated surface area, wherein said illuminated surface area is larger than about 1.5 mm$^2$, wherein said first beam of light induces a first autofluorescence emission from said surface area and wherein said second beam of light induces a second autofluorescence emission, wherein said conduit further comprises means for receiving and directing said first autofluorescence emission and said second autofluorescence emission;
a spacer fixedly attached to said distal end to place said distal end in a position that is not touching said tissue;
a device adapted to record said first autofluorescence emission and said second au tofluorescence emission; and
means for comparing said first autofluorescence emission and said second autofluorescence emission to assess in real-time a property of said tissue.

28. The apparatus of claim 27, wherein said first substantially narrow band and said second substantially narrow spectral band source comprise a laser that can emit a wavelength of at least 250 nm.

29. The apparatus of claim 27, wherein said laser is a commercially available compact laser.

30. The apparatus of claim 29, wherein said compact laser comprises a laser diode.

31. The apparatus of claim 27, wherein at least one of said first substantially narrow spectral band source and said second substantially narrow spectral band source are produced from a broad band optical lamp designed to transmit predetermined filtered wavelengths.

32. The apparatus of claim 27, wherein said first autofluorescence emission and said second autofluorescence from said tissue are within a spectral band between about 400 nm and about 1000 nm.

33. The apparatus of claim 27, wherein said first autofluorescence emission and said second autofluorescence from said tissue are within a spectral band between about 290 nm and about 800 nm.

34. The apparatus of claim 27, wherein said first autofluorescence emission and said second autofluorescence comprise an emission from a biological fluorophore.

35. The apparatus of claim 27, wherein at least one of said first substantially narrow spectral band source and said second substantially narrow band source provides a wavelength within the absorption spectrum of NADH.

36. The apparatus of claim 27, wherein at least one of said first substantially narrow spectral source and said second substantially narrow band source provides a wavelength within the absorption spectrum of tryptophan.

37. The apparatus of claim 27, further comprising means for hyperspectral microscopy to image tissue microstructure and assess microscopic alterations associated with injury of said tissue.

38. The apparatus of claim 27, wherein said tissue is in a state of ischernia.

39. The apparatus of claim 27, wherein said tissue is in a state of hypoxia.

40. The apparatus of claim. 27, wherein said first beam and said second beam comprise polarized light.

41. The apparatus of claim 27, wherein said first beam and said second beam are linearly polarized and a parallel-polarized component of at least one of said first autofluorescence emission -and said second autofluorescence emission is analyzed.

42. The apparatus of claim 41, wherein a perpendicularly polarized component of said first autofluorescence emission and said second autofluorescence emission is analyzed.

43. The apparatus of claim 27, wherein one of said first autofluorescence emission or said second autofluorescence emission comprises an opposite circular polarization orientation with respect to at least one of said first beam or said second beam, wherein said apparatus further comprises means for analyzing said opposite circular polarization orientation.

44. The apparatus of claim 27, wherein at least one of said first beam and said second beam comprises an elliptically polarized orientation, wherein said apparatus further comprises means for analyzing said elliptically polarized orientation.

45. The apparatus of claim 44, wherein at least one of said first beam or said second beam comprise an orthogonal elliptical polarization orientation, wherein said apparatus further comprises means for analyzing said orthogonal elliptical polarization orientation.

46. The apparatus of claim 27, wherein at least one of said first beam and said second beam is polarized and produces scattered electromagnetic radiation, wherein said apparatus further comprises means for analyzing said scattered electromagnetic radiation.

47. The apparatus of claim 46, wherein said scattered electromagnetic radiation comprises an orthogonal polarization component, wherein said apparatus further comprises means for analyzing said orthogonal polarization component.

48. The apparatus of claim 27, wherein said device comprises a charge coupled device.

49. The apparatus of claim 27, wherein said device comprises at least one detector selected from the group consisting of a photomultiplier and a photodiode.

50. The apparatus of claim 27, wherein said tissue is selected from the group consisting of brain, kidney, liver, heart, bowel, stomach, skin, pancreas, and muscle.

51. The apparatus of claim 27, wherein said conduit comprises an optical fiber bundle.

52. The apparatus of claim 51, wherein said fiber bundle comprises at least one illumination fiber having a diameter between about 500 microns and about 1 mm.

53. The apparatus of claim 52, wherein said illumination transporting optic is arranged to illuminate said tissue in a long dimension of up to about 10 cm.

54. The apparatus of claim 51, wherein said means for receiving and directing comprises one or more optical fibers having distal ends fixedly positioned adjacent to said distal end of said illumination transporting optic.

* * * * *

UNITED STATES PATENT AND TRADEMARK OFFICE
CERTIFICATE OF CORRECTION

PATENT NO. : 7,587,236 B2  Page 1 of 1
APPLICATION NO. : 11/031936
DATED : September 8, 2009
INVENTOR(S) : Stavros Demos et al.

It is certified that error appears in the above-identified patent and that said Letters Patent is hereby corrected as shown below:

Title Page;
(73) Assignee: change "Lawrence Livermore National Security, LLC, Livermore, CA (US)" to --Lawrence Livermore National Security, LLC, Livermore, CA (US) and the Regents of the University of California, Oakland, CA (US)--

Signed and Sealed this
Sixth Day of September, 2011

David J. Kappos
*Director of the United States Patent and Trademark Office*